United States Patent [19]
Spencer et al.

[11] Patent Number: 5,947,890
[45] Date of Patent: Sep. 7, 1999

[54] APPARATUS AND IMPROVED METHOD FOR SAFELY DISPENSING AND DELIVERING LIQUID RADIATION FOR INTRALUMINAL RADIATION THERAPY

[76] Inventors: Robert H. Spencer; Linda S. Spencer, both of 9107 Hemingway Grove Cir., Knoxville, Tenn. 37922

[21] Appl. No.: 08/933,819

[22] Filed: Sep. 19, 1997

[51] Int. Cl.⁶ ...................................................... A61N 5/00
[52] U.S. Cl. .................................. 600/3; 600/5; 600/435
[58] Field of Search ..................................... 600/1–8, 431, 600/432, 435; 604/181, 183, 184, 188, 191, 199, 213, 236; 206/570, 571, 363, 364, 365, 380, 438

[56] References Cited

U.S. PATENT DOCUMENTS

| | | |
|---|---|---|
| 4,332,254 | 6/1982 | Lundquist . |
| 4,740,203 | 4/1988 | Hoskins . |
| 5,059,166 | 10/1991 | Fischell et al. . |
| 5,165,540 | 11/1992 | Forney . |
| 5,201,725 | 4/1993 | Kling . |
| 5,242,432 | 9/1993 | DeFrank . |
| 5,300,034 | 4/1994 | Behnke et al. . |
| 5,302,168 | 4/1994 | Hess . |
| 5,336,180 | 8/1994 | Kriesel et al. . |
| 5,354,275 | 10/1994 | Behnke et al. . |
| 5,360,413 | 11/1994 | Leason . |
| 5,395,352 | 3/1995 | Penny . |
| 5,400,500 | 3/1995 | Behnke et al. . |
| 5,429,606 | 7/1995 | Robinson . |
| 5,460,439 | 10/1995 | Jennrich . |
| 5,474,544 | 12/1995 | Lawrence . |
| 5,503,613 | 4/1996 | Weinberger . |
| 5,549,566 | 8/1996 | Elias . |
| 5,549,651 | 8/1996 | Lynn . |
| 5,567,025 | 10/1996 | Haag, III . |
| 5,573,516 | 11/1996 | Tyner . |
| 5,616,114 | 4/1997 | Thornton et al. . |
| 5,616,129 | 4/1997 | Mayer . |

*Primary Examiner*—John P. Lacyk
*Attorney, Agent, or Firm*—Pitts & Brittian, P.C.

[57] ABSTRACT

The present invention first relates to an apparatus for dispensing liquid radiation for intraluminal radiation therapy. The apparatus uses two arms of a three-way stopcock to permanently connect a balloon-tipped catheter with an inflation syringe. The inflation syringe is fabricated from material which substantially limits radiation exposure. The apparatus is then placed into a sterile and closed catheter package comprised of a tray and a removable cover. The tray includes a port fashioned into its side, which receives the third arm of the three-way stopcock. Through this port, a radiopharmacist may inject liquid radiation into the inflation syringe while the apparatus remains within the sterile catheter package. In this manner, the medical staff are not required to load liquid radiation into the catheter assembly in the operating room, and may thereby avoid the risk of spillage and the risk of exposure to radiation incident to the loading process.

An improved method for delivering liquid radiation for intraluminal radiation therapy is also presented. Liquid radiation is loaded into the catheter assembly described above by the radiopharmacist at the radiopharmacy. The assembly is then transported to the operating room in a carrying case which is impermeable to radiation. In this manner, the operating team, the hospital personnel, and the visiting public are not exposed to radiation. Intraluminal radiation therapy may then be administered using the apparatus of the present invention.

17 Claims, 6 Drawing Sheets

APPARATUS AND IMPROVED METHOD FOR SAFELY DISPENSING AND DELIVERING LIQUID RADIATION FOR INTRALUMINAL RADIATION THERAPY

TECHNICAL FIELD

This invention relates generally to intraluminal radiation therapy. An example of intraluminal radiation therapy to be addressed herein is Intravascular Radiation Therapy (IRT) such as would be performed by physicians during percutaneous transluminal angioplasty (PTA). More specifically, this invention pertains to an apparatus and method for dispensing and delivering liquid radiation for intraluminal radiation therapy so as to reduce radiation exposure to the medical staff and patient.

BACKGROUND ART

The interventional procedure known as "percutaneous transluminal angioplasty" (PTA) is commonly employed to treat arterial stenosis. In the conventional PTA procedure, a preshaped guide wire is introduced into an artery and advanced until the distal end of the guidewire is beyond the point of arterial buildup. A balloon-tipped catheter is then pushed over the guide wife until the balloon resides within the narrowed portion of the artery. The balloon is inflated in order to compress arterial buildup against the inner wall of the artery so as to allow the unrestricted flow of blood.

PTA, or "balloon surgery" as it is sometimes known, is the primary treatment for intravascular stenosis. In the context of coronary arteries, the procedure is referred to as percutaneous transluminal coronary angioplasty, or PTCA. Approximately 600,000 balloon angioplasty procedures are performed in the United States annually, consuming $5,000,000,000.00 of health care resources. Percutaneous transluminal coronary angioplasties represent 400,000 of these procedures.

PTA and PTCA have enjoyed a high success rate for correcting arterial blockage. These procedures are much less invasive than bypass surgery. Unfortunately, arteries which have undergone balloon angioplasty have demonstrated a propensity towards restenosis. As discussed in U.S. Pat. No. 5,616,114 to Thornton, et al, restenosis occurs "as a result of injury to the arterial wall during the lumen opening angioplasty procedure." Injury to the arterial wall stimulates hyperplastic growth of the vascular smooth muscle cells. It is this smooth muscle growth that renarrows the vessel lumen, necessitating a repeat angioplasty or, perhaps, surgical revascularization.

A procedure in development for reducing the restenosis rate is the introduction of radiation energy into the interior of the vessel. This procedure, known alternately as Intravascular Radiation Therapy (IRT) or brachytherapy, has been shown to inhibit fibroblast and smooth muscle cell hyperplasia. Various methods for introducing radiation into an area treated for stenosis are known. Some methods deliver radiation in a solid medium, while others utilize liquid sources.

U.S. Pat. No. 5,059,166 to Fischell discloses an IRT method that relies on a radioactive stent that is permanently implanted in the blood vessel after completion of the lumen opening procedure. U.S. Pat. No. 5,302,168, issued to Hess, teaches use of a radioactive source contained in a flexible catheter with remotely manipulated windows. U.S. Pat. No. 5,503,613 to Weinberger uses a liquid filled balloon to guide a solid source wire to a treatment site. U.S. Pat. No. 5,616,114, to Thornton, et al, describes an apparatus and method, for delivering liquid radiation into a balloon-tipped catheter. In Thornton's method, expansion of the balloon by injection of the radioactive liquid serves the dual function of expanding the blockage and relieving the stenosis, while at the same time irradiating the tissue. Finally, it is known in the art to transiently place seeds of a radioactive substance into the vessel by means of a wire.

The use of radioactive materials in connection with an angioplasty procedure creates a risk of harmful exposure, both to the medical personnel and to the patient. Precautionary measures have been incorporated to protect against the leakage of liquid radiation into the blood stream during angioplasty. See, for example, U.S. Pat. No. 5,616,114, to Thornton, et al. wherein a closed catheter system is employed. However, the prior art fails to disclose an apparatus by which medical staff and patients can be shielded from radiation prior to the introduction of the radioactive substance into the catheter.

In the context of liquid IRT, the known procedure for introducing radiation into an angioplasty catheter is by loading liquid radiation into a bore syringe. The syringe, in turn, is placed in fluid communication with the balloon-tipped catheter. Various radiation sources have been used for IRT. Examples of these include Strontium 90 ($^{90}$Sr), Iridium 192 ($^{192}$Ir), Phosphorous 32 ($^{32}$P), Rhenium 186 ($^{186}$Re) and Rhenium 188 ($^{188}$Re). However, it is appreciated that all of these sources emit radiation which presents a risk of harm from exposure.

The apparatus and method employed by medical staff today to provide shielding from radiation is use of a lead apron. The operator of the angioplasty assembly and the assisting medical staff are draped in aprons which are impermeable to radiation. However, it is evident to those skilled in the medical art that the lead apron does not insulate radiation within the angioplasty catheter assembly; rather, it only shields those parts of the body covered by the lead apron. Uncovered parts such as the hands and face remain exposed. Exposure to radiation is exacerbated by the process employed to load radiation into an angioplasty catheter assembly. First, the operator is required to manually load the radioactive liquid into the inflation syringe. This creates a hazard of exposure to radiation emanating from the syringes, and also creates a risk that the operating field may become contaminated in the event of a leak during the loading process. Second, there is a risk of leakage during the process of irradiating tissue, Those skilled in the art will appreciate that the connectors used to connect the inflation syringe with the other parts of the angioplasty catheter assembly are detachable and may become disconnected.

An apparatus and method are needed which will protect the medical staff and patient from radiation exposure during the angioplasty procedure. The prior art fails to disclose an apparatus by which medical staff and patients can be shielded from radiation emanating from the angioplasty catheter assembly during IRT. Medical packages such as the one disclosed in U.S. Pat. No. 5,165,540, to Forney, Y-adaptors such as the one disclosed in U.S. Pat. No. 5,395,352 to Penny, and inflation syringes such as the one disclosed in U.S. Pat. No. 5,429,606, all of which have utility to the operation of an angioplasty catheter, do not work together to speak to or teach an apparatus which will shield the medical staff and patient from radiation. Additionally, prior art fails to teach an apparatus and method by which radioactive liquid can be loaded into an angioplasty syringe at the radiopharmacy, and then transported to the operating room in a sterile and radiation shielded manner.

It is an object of the present invention to provide a catheter assembly having nondetachable connections so as to reduce the risk of leakage of liquid radiation during the radiation injection process.

It is also an object of the present invention to provide a sterile package for a catheter assembly which provides a unique injection port through which liquid radiation may be loaded by the radio-pharmacist at the pharmacy into an inflation syringe. In this manner, the catheter operator is not required to transfer liquid radiation during angioplasty. This removes the risk of exposure to the medical staff and patient during the delicate loading process. It further avoids the risk that radioactive liquid might fall onto the angioplasty table or elsewhere, thereby contaminating the operating field.

It is further an object of the present invention to provide an inflation syringe for injecting liquid radiation into a catheter, wherein the syringe is fabricated to limit radiation exposure.

Finally, it is an object of the present invention to provide a method for performing intraluminal radiation therapy which includes the use of radiation insulated carrying cases which allow the transportation of the loaded angioplasty catheter assembly from the radiopharmacy to the operating room in a sterile and radiation shielded environment, and from the operating room to an appropriate disposal site.

DISCLOSURE OF THE INVENTION

Other objects and advantages will be accomplished by the present invention which provides an apparatus and improved method for safely dispensing and delivering liquid radiation in connection with intraluminal radiation therapy. The apparatus first presents a container for holding an angioplasty catheter assembly. The container defines a sterile package comprising a tray and a removable cover. Both the tray and the removable cover are water-resistant. The package also has an injection port for receiving liquid radiation from an external loading syringe.

Within the sterile package rests an entire angioplasty catheter assembly. The assembly first includes a three-way stopcock. This is a stopcock having three ports, and a valve for controlling the flow of liquid radiation through the ports. In the present invention, one port of the stopcock serves as an inlet port. This port is placed in the injection port of the sterile package and receives liquid radiation from the external loading syringe. The other two ports are outlet ports, namely, a syringe port and a catheter port.

The syringe port of the three-way stopcock connects to an inflation syringe having a locking plunger. The catheter port connects to a balloon-tipped catheter. The valve of the three-way stopcock is positioned so as to place the inlet port and the syringe port in fluid communication. In addition, the plunger is partially retracted from the bore of the syringe so as to pull a vacuum within the assembly. In this manner, the injection of liquid radiation through the injection port will cause the radioactive liquid to travel into the bore of the inflation syringe.

Safety features are incorporated into the catheter assembly. First, the syringe is fabricated in such a manner as to limit the penetration of radiation so as to reduce exposure to medical staff and the patient. Second, the connections within the assembly are nondetachable so as to reduce the risk of leakage of liquid radiation. Third, a removable port cover is placed over the injection port of the package until the time when liquid radiation is loaded into the catheter assembly. After liquid radiation is loaded, a package cap is provided to cover the injection port of the sterile package. Finally, a stopcock cap is provided. The stopcock cap is placed over the inlet port after the assembly is removed from the sterile package. This prevents radiation from escaping from the catheter assembly through the inlet port.

In accordance with the present invention, the package containing the angioplasty catheter assembly is maintained at a radiopharmacy. Before an intraluminal radiation therapy procedure is to begin, the radio-pharmacist loads liquid radiation into the inflation syringe through the injection port and the three-way stopcock. The loaded apparatus is then transported to the operating field by use of a properly labeled radiation insulated carrying case. Once at the operating field, the apparatus is removed from the carrying case, and the catheter assembly is taken out of the sterile package. At that point, the angioplasty procedure, including intravascular radiation therapy, may commence.

After the procedure is accomplished, the apparatus must be properly disposed. A second properly-labeled carrying case is employed to transport the contaminated angioplasty catheter assembly, with the radioactive liquid inside, to a suitable biohazardous and radioactive disposal site.

BRIEF DESCRIPTION OF THE DRAWINGS

The above mentioned features of the inventions will become more clearly understood from the following detailed description of the inventions read together with the drawings in which.

DESCRIPTION OF PREFERRED EMBODIMENT

Figure 1:
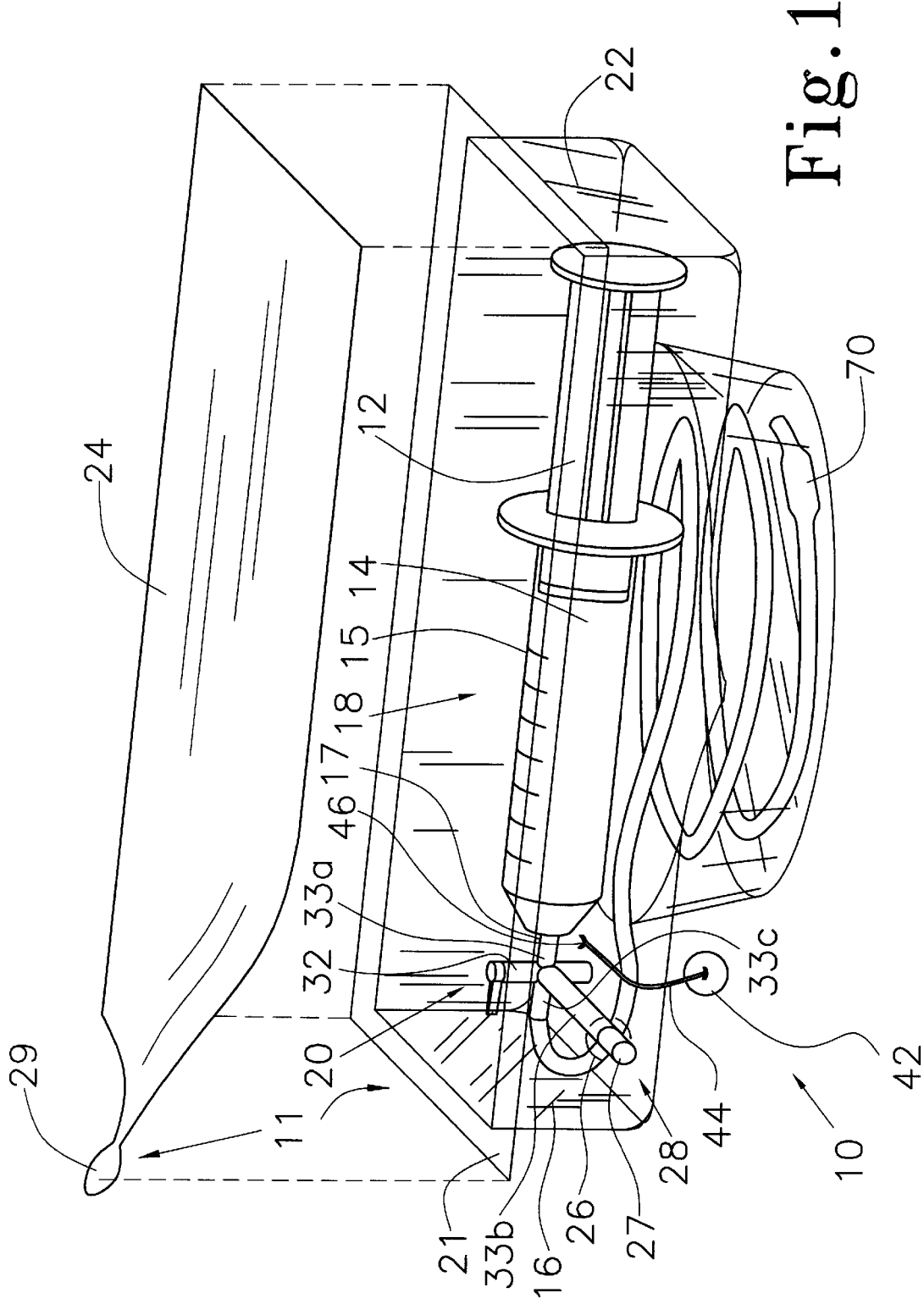
FIG. 1 is a perspective view of a catheter assembly and package of the present invention, with the injection port cover removed from the port.
Figure 2:
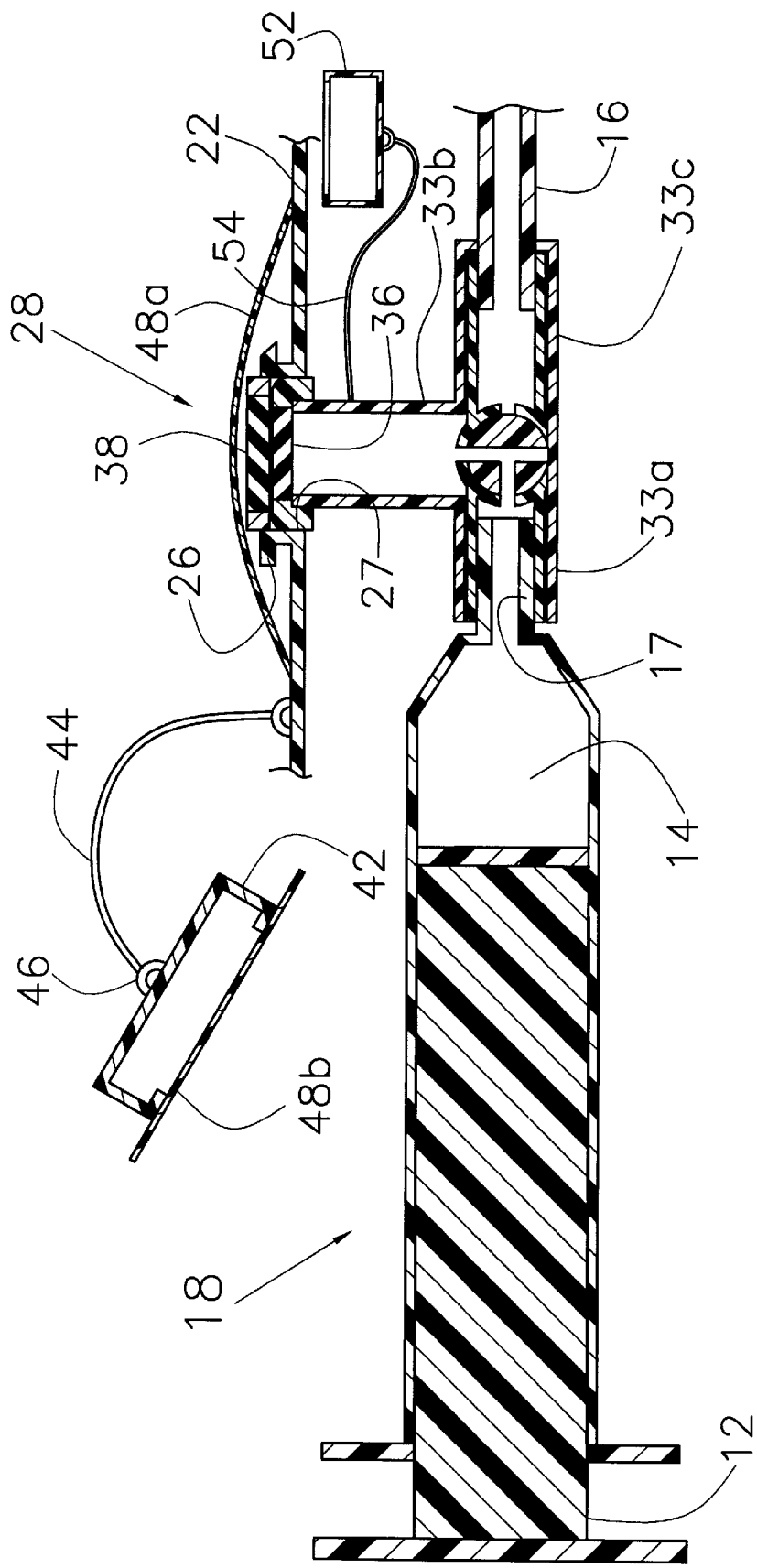
FIG. 2 is a cross-section of an inflation syringe in fluid communication with a three-way stopcock valve and injection port of the present invention.
Figure 3:
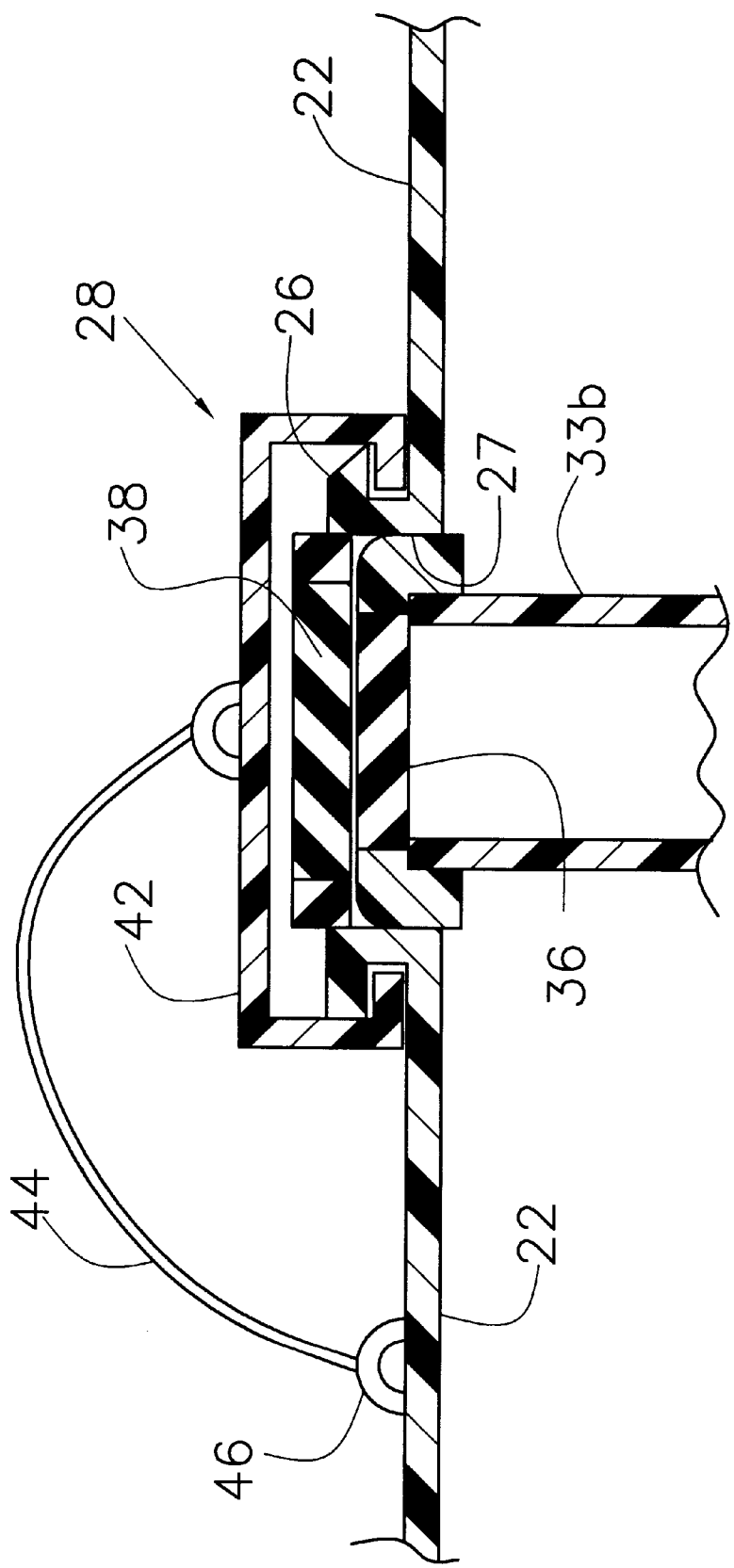
FIG. 3 is a side view, in cross-section, of the injection port in the package of the present invention, with the port cap in place over the injection port.

A preferred embodiment of the apparatus of the present invention is shown generally at 10 in the perspective view of FIG. 1. FIG. 1 presents an apparatus consisting of a closed angioplasty catheter assembly within a, sterile package.

The package at 11 defines a tray 22 having a package port 27 and a cover 24. The tray 22 is fabricated from a material which is impermeable to liquid. In the preferred embodiment, the tray 22 is made of semi-rigid plastic, and is configured to hold the angioplasty catheter assembly 20. More specifically, the tray 22 is formed to closely hold the angioplasty catheter assembly 20 so that it does not become repositioned within the tray 22, it being important that the catheter assembly 20 not become detached from the package port 27.

A desirable feature of the tray 22 is that it be fabricated from a transparent material. In the preferred embodiment, a clear plastic is provided. This allows the radio-pharmacist to visually confirm that liquid radiation has entered the bore 14 of the syringe 18 without opening the package 11. It also serves the even more basic function of providing visual confirmation as to the contents within the package 11 before radioactive liquid is injected therein.

Positioned on the tray 22 is the cover 24. As with the tray 22, the cover 24 is impermeable to liquid. In the preferred embodiment, the cover 24 is fabricated from water-resistant paper, a common covering substance for the packaging of medical equipment. However, it is understood that other materials such as flexible plastic may serve as a cover 24.

To maintain sterility within the package 11, the cover 24 must sealingly fit onto or over the top of the tray 22. FIG. 1 shows the cover 24 attachable to a horizontal lip 21 at the top of the tray 22. Attachment is by means of a typical adhesive. In the preferred embodiment, the cover 24 may be removed simply by peeling it off of the lip 21. This is facilitated by providing a short flap 29 extending from one corner of the cover 24. Those skilled in the art will understand that, in order to maintain sterility, the cover 24 is not to be removed until the package 11 is in the sterile field of the operating room.

Within the sterile package 11 of the present invention resides the angioplasty catheter assembly 20. The catheter assembly 20 first comprises an inflation syringe 18 having an internal bore 14 and a plunger 12. Numerous inflation syringes are known in the medical field. In the context of angioplasty, these syringes receive a solution comprised of saline and contrast. The solution is then injected into a balloon-tipped catheter 70 positioned in the patient's blood vessel. For IRT, the inflation syringe 18 receives a solution of liquid radiation and contrast from an external loading syringe 50. The radiation is then injected into the dilating balloon 70 in accordance with angioplasty procedures.

The package 11 of the present invention can be used in conjunction with known inflation syringe configurations. However, the present invention offers an improved inflation syringe 18 which differs from syringes already known in that a three-way stopcock 32 is permanently attached to the tip 17 of the inflation syringe 18. This means that arm 33a of the stopcock 32 is placed in sealed and permanent fluid communication with the syringe 18 via the syringe tip 17.

To provide additional protection to the user and other individuals in the operating room, the connection between the stopcock 32 and the inflation syringe 18 is nondetachable. This reduces the risk of a leak of liquid radiation from the connection. In addition, the wall 15 of the syringe 18 is fabricated from a material chosen to limit exposure to radiation. Various materials are known to be radiation inhibiting, such as plastic and quartz. It will be understood by those skilled in the art that the wall thickness of the syringe 18 is also chosen to limit radiation exposure. This is because wall thickness is a function of both the material used and the isotope contained in the syringe 18. For example, if the isotope is Rhenium 188, a transparent plastic composition having a wall thickness of at least 1 cm (0.3937 inches) is appropriate.

The angioplasty catheter assembly 20, of course, also has a catheter 16. In the preferred embodiment, the catheter 16 is a closed, dilation balloon catheter as is used in performing PTA and/or PTCA. The catheter 16 is attached to the second arm 33c of the three-way stopcock valve 32. The attachment, again, is sealed and permanent, such as through unitary construction, so as to avoid the risk of a leak of liquid radiation 20.

Figure 4:
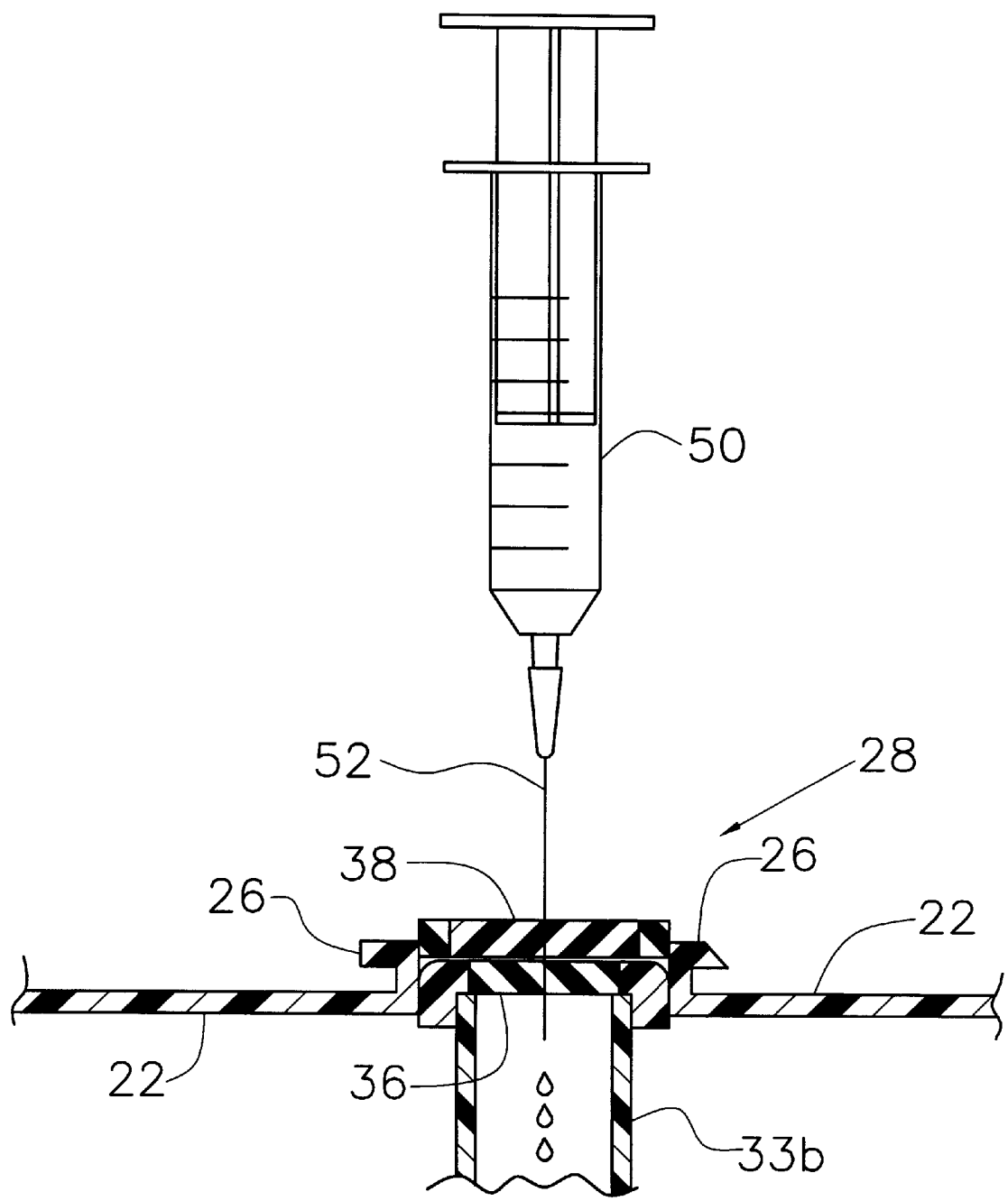
FIG. 4 is a side view of a liquid radiation syringe injecting liquid radiation into the package of the present invention, with the package, membranes, and stopcock arm in cross-section.

As mentioned, the package 11 in FIG. 1 also includes a package port 27. The package port 27 is fabricated into a side of the tray 22, and is positioned in the package 11 so as to receive the third arm 33b of the three-way stopcock 32. The package port 27 is configured to sealingly receive arm 33b of the stopcock 32. This enables the package port 27 to serve as an injection port 28 through which liquid radiation may be loaded into the catheter assembly 20 while the assembly resides within the sterile package 11. (See FIG. 4.) In the preferred embodiment, the package port 27 is one of several parts which serve together as an injection port 28. The injection port 28 includes receiving arm 33b of the stopcock 32. Within arm 33b resides a membrane 36. Membrane 36 receives an injection from an injection syringe 50 having a needle 52. The needled injection syringe 50 serves as the external source for liquid radiation. Of course, those skilled in the art will understand that needleless injection membranes may be used to receive a needleless injection.

In order to maintain sterility within the package 11 and the catheter assembly 20, a second membrane 38 is placed within the injection port 28. This membrane 38 resides within package port 27, and covers the membrane 36 within stopcock arm 33b. As with membrane 36, membrane 38 is configured to receive an injection syringe 50 having a needle 52. While a needled injection syringe is preferred, it is again recognized that a needleless system for loading liquid radiation may be employed as well.

As presented in FIG. 1, membrane 38 is exposed to the environment. In order to maintain sterility of the apparatus 10, some means of covering port 28, including membrane 38, is needed. In the preferred embodiment, this is accomplished by placing a section of removable paper 48a over the injection port 28 before the apparatus 10 is used. As with the tray cover 24, the port cover 48a is fabricated from lined paper impermeable to fluid, and is sealed over the injection port 28 by an adhesive. The port cover 48a is removed by simply peeling it away from the port 28.

In accordance with the present invention, liquid radiation is injected into inflation syringe 18 by the radiopharmacist at the pharmacy site. This is done by the use of an external loading syringe 50. To accomplish this, port cover 48a must first be removed from the injection port 28.

In order for the apparatus 10 of the present invention to operate optimally, negative pressure must exist within the catheter assembly 20. Negative pressure can be achieved first by rotating the valve 34 of the stopcock 32 to one of its open positions so as to place arm 33a of the stopcock 32 in fluid communication with arm 33b. The plunger 12 of the inflation syringe 18 is then partially retracted from the bore 14 so as to pull a vacuum. This, of course, is done before the catheter assembly 20 is sealed within the sterile package 11. The resulting vacuum will bias the injected liquid radiation to travel through the stopcock 32 and into the bore 14 of the syringe 18.

After the port cover 48a has been removed and the liquid radiation loaded into the inflation syringe 18, a second means is needed to maintain sterility of the injection port 28. This is accomplished in the preferred embodiment by a package cap 42. The package cap 42 defines a plastic or other semi-rigid material having an inwardly flanged shoulder. The package cap 42 is configured to snap over and around a lip 26 extending up from the package port 27. In the preferred embodiment, the port lip 26 is actually molded into the tray 22.

In order to assist the radiopharmacist and the catheter operator, the preferred embodiment provides for the package cap 42 to be tethered to the tray 22. A tethering ring 46 is fabricated into the tray 22 to attach to the tether 44. Tethering allows for quick retrieval and placement of the package cap 42 so as to preserve sterility of the catheter assembly 20.

An additional feature is incorporated into the package cap 42 to aid in sterility. This feature is a removable cap cover 48b. As with port cover 48a, cap cover 48b is a section of lined, water-resistant paper, which is sealed over the bottom of the port 28 by an adhesive. The cap cover 48b is removed by simply peeling it away from the cap 42 itself The package cap 42 can then be placed over the package port 27 following loading of liquid radiation into the catheter assembly 20.

Those skilled in the art will readily see that the package cap 42 may take other embodiments. For example, the package cap 42 might be an internally threaded cover which screws onto an externally threaded radial mount (not shown). Alternatively, the package cap 42 might simply be a piece of lined paper having adhesive edges (not shown) which is placed over the package port 27.

An additional feature is also provided within the catheter assembly 20 of the present invention to further shield the patient and medical staff from radiation exposure. That feature is a stopcock cap 52. As with the package cap 42, the stopcock cap 52 defines a plastic or other semi-rigid material having an inwardly flanged shoulder. The stopcock cap 52 is configured to fit over arm 33b of the stopcock 32. In the preferred embodiment, a frictional fit is employed, though any conventional connection means is acceptable. A tether 54 is also provided to conveniently place the stopcock cap 52 in convenient proximity to arm 33b. The stopcock cap 52 is placed over arm 33b of the stopcock 32 after the catheter assembly 20 is removed from the sterile package 11.

The apparatus 10 of the present invention is designed to allow the operating room staff the ability to perform intraluminal radiation therapy with minimal exposure to radiation. This is accomplished by having the inflation syringe 18 loaded at the radiopharmacy site rather than in the operating room. The radiopharmacist removes the port cover 48a from the port 48, and then injects the appropriate amount of radioactive liquid into the syringe 18.

After loading the syringe 18, the pharmacist peels the cap cover 48b from the bottom of the cap 42,. The cap 42 is then snapped in place over the package port 27 to preserve sterility of the membrane 38. The cap 42 also reduces radiation exposure to those in proximity to the package 11. At that point, the loading process is completed.

Figure 5:
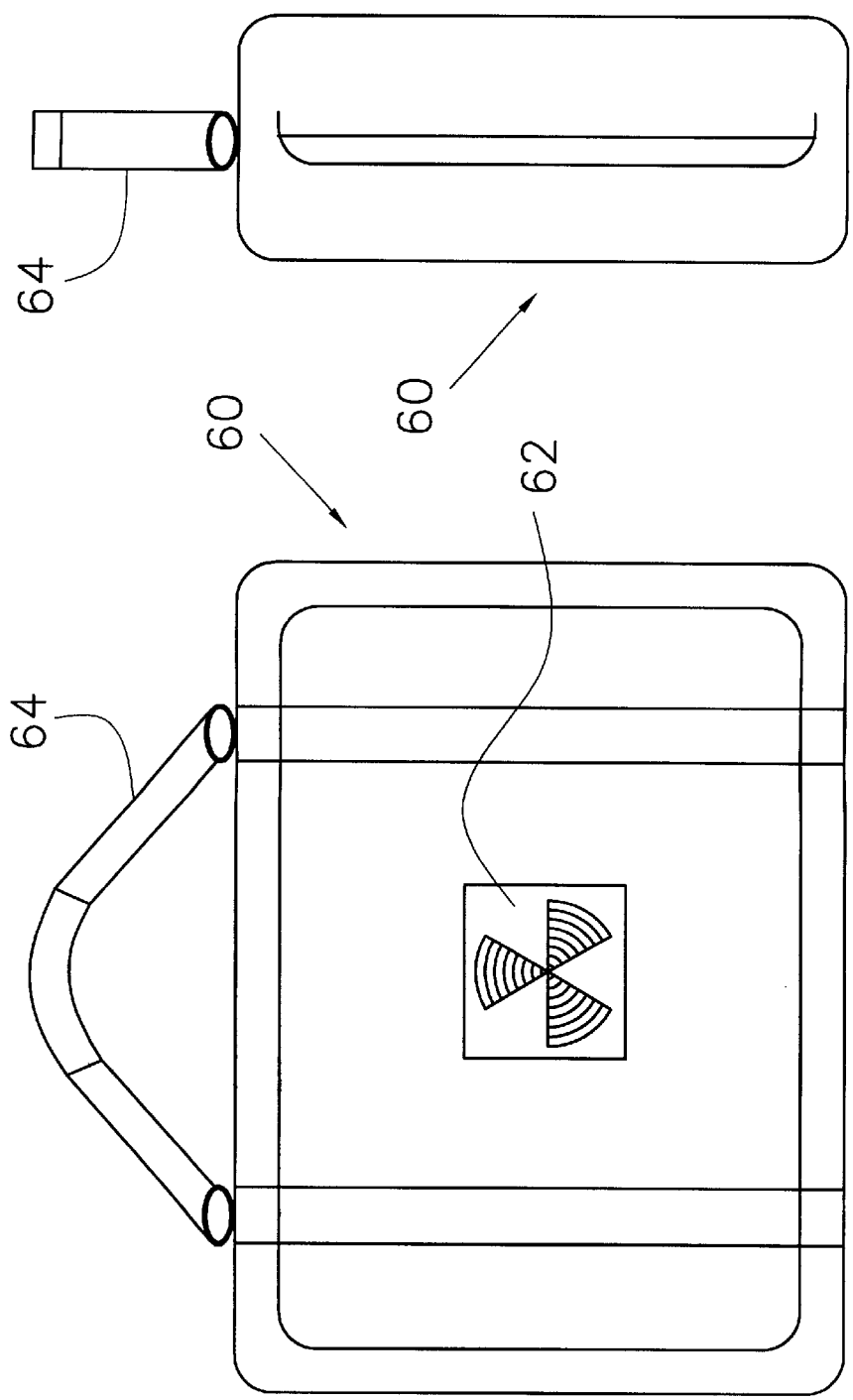
FIG. 5a depicts an elevation view of a side of a radiation shielded carrying case useful for carrying an angioplasty catheter assembly and package of the present invention.
FIG. 5b depicts an elevation view of an end of a radiation shielded carrying case useful for carrying an angioplasty catheter assembly and package of the present invention.

The loaded apparatus 10 must next be transported to the operating room. In the interest of safety, a shielded carrying case 60 is provided. The carrying case, depicted in FIG. 5a and FIG. 5b, is configured to hold the apparatus 10 of the present invention in its fully loaded state. In other words, an angioplasty catheter assembly 20 and package 11, such as presented in FIG: 1, is completely held within the carrying case 60. Such a case 60 allows the radiopharmacist or other hospital personnel to deliver to the operating room a preloaded angioplasty catheter assembly 20, without fear of radiation exposure to hospital staff and visitors.

The material of the carrying case 60 is sturdy so as to protect the contents from damage. It is also light in weight to allow any hospital personnel to transport it by hand. The carrying case 60 has a handle 64 and a latching or locking mechanism (not shown), as well as a lining, such as lead, for shielding radiation. Finally, the carrying case 60 should bear a conventional label 62 indicating the presence of radioactive material.

Upon delivery of the carrying case 60 and its contents to the operating room, the apparatus 10 is removed. The user peels the cover 24 from the tray 22 of the package 11. He or she may then remove the sterile angioplasty catheter assembly 20 from the package 11 and commence the angioplasty procedure. Because the catheter assembly 20 is closed, and because the inflation syringe 18 is fabricated from a material to limit radiation exposure as disclosed above, removal of the catheter assembly 20 from the package 11 does not significantly expose the medical staff and patient to radiation.

Those skilled in the art will understand that the conventional angioplasty catheter assembly will include a pressure gauge (not shown). The gauge is necessary to ensure that excess pressure is not applied by the inflation syringe 18 upon the balloon 70. It is also necessary that there be a means for calculating dosage of radiation. Dosage is a factor of several variables, including the size of the balloon 70 and the nature of the radio-isotope in the liquid radiation. The operator must have knowledge of the data for these variables, and the ability to make the dosage calculation. To assist in this, a calculator (not shown) may be provided which stores data pertaining to these variables. The data is entered by the radiopharmacist at the radiopharmacy, with the calculator then being delivered to the catheter assembly operator along with the loaded catheter assembly 20 itself Once dosage is calculated, the patient's intraluminal site may be appropriately irradiated. This requires that the plunger 12 of the inflation syringe 18 be advanced in order to force liquid radiation into the catheter 16. In order to direct the liquid radiation into the catheter 16, the valve 34 of the stopcock 32 must be oriented to place the bore 14 of the syringe 18 in fluid communication with the catheter 16 only.

Figure 6:
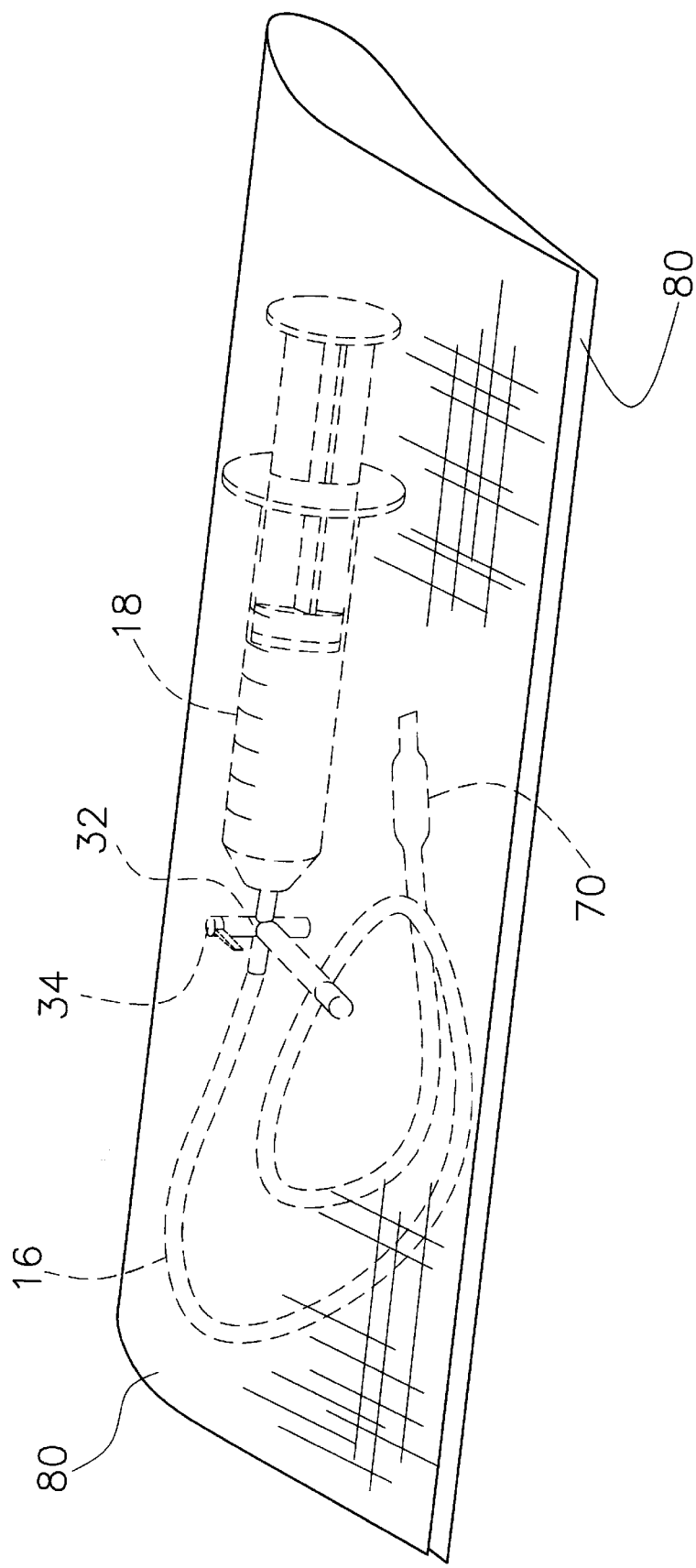
FIG. 6 depicts a catheter assembly enveloped by a lead shield.

Those skilled in the art will note that injection of the liquid radiation from the inflation syringe 18 into the catheter 16 will cause radioactive liquid to no longer be substantially insulated. This is because the catheter 16 itself is not impermeable to radiation. However, the stream of radioactive liquid within the catheter 16 is extremely thin, and radio-isotopes emanating therefrom are essentially de minimus. It is, nevertheless, desirable to eliminate even this exposure. This can be accomplished by covering or surrounding the catheter 16 as it enters the patient with a conventional lead shield 80. Further, the entire catheter assembly 20 may be covered during the irradiation process so that the patient is not exposed to radiation beyond that placed within the luminal site. (See FIG. 6.)

After the irradiation process is completed, the liquid radiation must be withdrawn from the catheter 16. This, of course, is done, by retracting the plunger 12 within the bore 14 of the inflation syringe 18. Retracting the plunger 14 so as to fully remove the liquid radiation will create negative pressure within the catheter 16. At that point, the valve 34 of the stopcock 32 is rotated so as to preclude the entry of liquid radiation back through the stopcock 32. The angioplasty procedure is then completed and the catheter 16 is removed from the patient.

Federal regulations and conventional medical procedures require that the contaminated catheter assembly 20 be properly disposed of. This requires delivery of the equipment to an appropriate biohazardous and radioactive waste site. To accomplish this, the contaminated catheter assembly 20 is first placed into a conventional biohazardous waste bag (not shown). The bag and its contents are then placed into a second radiation insulated carrying case (also not shown) for transportation of the biohazardous waste bag. The second radiation shielded carrying case bears conventional labels for both radioactive material and biohazardous waste. Except for the additional label, the second case is substantially identical to the first in its dimensions and properties.

The description given above presents an apparatus and improved method for the sterile and safe delivery of radiation to blood vessels. It will be appreciated that this invention is highly versatile, being useful for the delivery of radiation to various luminal systems in the body. The foregoing apparatus and method are suitable for use with any balloon catheter device, whether mechanical, automatic, or manual. This includes multiple balloon systems. The present invention can be used in conjunction with stent systems and athrectomy systems. It is compatible with multi-modality technology where liquid radiation is used in conjunction with solid radiation, light radiation, video or ultrasound imaging, drug delivery or other combinations. Although it is described herein for use with intravascular therapy, it will be recognized by those skilled in the art that the present invention may be useful in localized radiotherapy of any selected portion of a patient's body lumen.

From the foregoing description, it will be recognized by those skilled in the art that an apparatus dispensing liquid radiation during intraluminal radiation therapy offering advantages over the prior art has been provided. First, an apparatus for dispensing liquid radiation during intraluminal radiation therapy is presented. The apparatus uses two arms of a three-way stopcock to permanently and fluidly connect a balloon-tipped catheter with an inflation syringe. The inflation syringe is fabricated from material which substantially limits radiation exposure. The apparatus is then placed into a sterile and closed catheter package comprised of a tray and a removable cover. The tray includes a port fashioned into its side, which receives the third arm of the three-way stopcock. Through this port, a radiopharmacist may inject liquid radiation into the inflation syringe while the apparatus remains within the sterile catheter package. In this manner, the medical staff is not required to load liquid radiation into the catheter assembly in the operating room, and may thereby avoid the risk of spillage and the risk of exposure to radiation incident to the loading process.

An improved method for delivering liquid radiation for intraluminal radiation therapy is also presented. Liquid radiation is loaded into the catheter assembly described above by the radiopharmacist at the radiopharmacy. The assembly is then transported to the operating room in a carrying case which is radiation shielded. In this manner, the operating team, the hospital personnel, and the visiting public are not exposed to radiation. Intraluminal radiation therapy may then be administered using the apparatus of the present invention. Along with this apparatus, a radiation insulating shield can be wrapped around the catheter assembly so as to further guard the patient and medical staff from radiation exposure.

While a preferred embodiment for the foregoing has been shown and described, it will be understood that the description is not intended to limit the disclosures, but rather is intended to cover all modifications and alternate methods falling within the spirit and the scope of the invention as defined in the appended claims.

Having thus described the aforementioned inventions, We claim:

1. A catheter package for containing a catheter assembly used to provide intraluminal radiation treatment, the catheter assembly including an inflation syringe having a bore which receives liquid radiation from a loading syringe, and a catheter in fluid communication with the bore of the inflation syringe, said package comprising:

a water proof tray comprising a base and at least one side wall having an upper surface, said water proof tray being configured to receive said catheter assembly in a substantially stable position;

a removable water proof cover configured to cover said base proximal to said upper surface of said side wall, thereby forming a sterile, internal chamber within said water proof tray and said removable water proof cover;

an injection port within said side wall configured to receive an injection of liquid radiation from the loading syringe;

a removable port cover to maintain the sterility of said injection port and said catheter package; and a connector placing said injection port in fluid communication with the bore of the inflation syringe.

2. The catheter package of claim 1 wherein said injection port further provides a membrane for receiving an injection of liquid radiation.

3. The catheter package of claim 2 wherein said removable port cover is a sterilized and detachable section of water-proof paper, said water-proof paper being adhesively attached to said side wall of said tray over said injection port.

4. The catheter package of claim 3 further comprising:

a detachable semi-rigid cap having a top surface and a bottom surface, said cap configured to cover said injection port after removal of said removable port cover;

a cap connector configured to receive said detachable semi-rigid cap at said injection port; and a sterilized and detachable section of water-proof paper adhesively attached to said bottom surface of said cap.

5. The catheter package of claim 4 wherein said detachable semi-rigid cap defines a radial, inward flange, and said cap connector defines a radial shouldered mounting piece, said cap being configured to snap onto said connector.

6. A catheter assembly as used to provide intraluminal radiation treatment wherein the catheter assembly receives liquid radiation from a loading syringe, and then delivers that radiation energy to intraluminal tissue, said catheter assembly comprising:

a catheter having a first end and a second end, said second end being fluidly connected to a balloon;

an inflation syringe fabricated from material which limits penetration of radiation, said inflation syringe having first and second ends, said first end slideably receiving a plunger, said inflation syringe further having a bore which fluidly connects said first and second ends and through which said plunger frictionally travels; and a three-way stopcock having an inlet port for receiving an injection of liquid radiation from the loading syringe, a syringe port nondetachably and fluidly connected to said second end of said inflation syringe, and a catheter port nondetachably and fluidly connected to said first end of said catheter, said three-way stopcock further having a valve for directing the flow of liquid radiation received from the loading syringe through said three-way stopcock.

7. The catheter assembly of claim 6 wherein the catheter assembly includes a sterilizeable package comprising:

a water proof tray comprising a base and at least one side wall having an upper surface, said water proof tray being configured to receive said catheter assembly in a substantially stable position;

a removable water proof cover configured to cover said base proximal to said upper surface of said side wall, thereby forming a sterile, internal chamber within said water proof tray and said removable water proof cover;

an injection port within said side wall for receiving an injection of liquid radiation from the loading syringe, said injection port sealingly receiving said inlet port of said three-way stopcock;

removable port cover to maintain the sterility of said injection port and said catheter package;

and wherein said valve of said stopcock is oriented to place said inlet port of said stopcock in fluid communication with said bore of said syringe only, and wherein said plunger has been partially withdrawn from said bore of said inflation syringe so as to pull a vacuum within said inflation syringe, thereby biasing the liquid radiation to travel into said bore of said syringe when injected from the loading syringe into said inlet port.

8. The catheter assembly of claim 7 wherein said inlet port of said three-way stopcock provides a membrane therein for receiving a needled injection.

9. The catheter assembly of claim 8 wherein said injection port contains a membrane for receiving a needled injection.

10. The catheter assembly of claim 7 wherein said tray is fabricated from transparent plastic formed to closely receive said catheter, said inflation syringe and said three-way stopcock so as to maintain said inflation syringe and said three-way stopcock in a substantially stable position relative to said injection port.

11. The catheter assembly of claim 7 wherein said removeable port cover is a sterilized and detachable section of water-proof paper, said paper being adhesively attached to said sterlizeable package over said injection port.

12. The catheter assembly of claim 7 wherein said sterilizeable package further comprises:

a detachable semi-rigid cap having a top surface and a bottom surface, said cap configured to cover said injection port after removal of said removable port cover;

a cap connector configured to receive said detachable semi-rigid cap at said injection port; and a sterilized and detachable section of water-proof paper adhesively attached to said bottom surface of said cap.

13. The catheter assembly of claim 12 wherein said detachable semi-rigid cap defines a radial, inward flange, and said cap connector defines a radial shouldered mounting piece, said cap being configured to snap onto said connector.

14. The catheter assembly of claim 12 wherein said detachable semi-rigid cap defines an internally threaded radial cap, and said connector defines an externally threaded radial mounting piece, said cap being configured to screw onto said connector.

15. The catheter assembly of claim 7 wherein said inlet port of said three-way stopcock and said injection port of said sterilizeable package receive a needleless injection of liquid radiation from the loading syringe.

16. A catheter assembly as used to provide intraluminal radiation treatment wherein the catheter assembly receives liquid radiation from a loading syringe, and then delivers that radiation energy to intraluminal tissue, said catheter assembly comprising:

a catheter having a first end and a second end, said second end being fluidly connected to a balloon;

an inflation syringe fabricated from material which limits penetration of radiation, said inflation syringe having first and second ends, said first end slideably receiving a plunger, said inflation syringe further having a bore which fluidly connects said first and second ends and through which said plunger frictionally travels;

a three-way stopcock having an inlet port for receiving an injection of liquid radiation from the loading syringe, a syringe port nondetachably and fluidly connected to said second end of said inflation syringe, and a catheter port nondetachably and fluidly connected to said first end of said catheter, said three-way stopcock further having a valve for directing the flow of liquid radiation received from the loading syringe through said three-way stopcock, said valve being oriented to place said inlet port of said stopcock and said bore of said syringe in fluid communication, and wherein said plunger of said inflation syringe has been partially withdrawn from said bore of said inflation syringe so as to pull a vacuum within said inflation syringe, thereby biasing the liquid radiation to travel into said bore of said syringe when injected from the loading syringe into said inlet port;

a membrane within said inlet port of said stopcock for receiving a needled injection of liquid radiation from the loading syringe;

a stopcock cap configured to cover said inlet port of said stopcock, said stopcock cap being fabricated from material which limits penetration of radiation, and said stopcock cap being placed over said inlet port of said stopcock during intraluminal radiation therapy;

a sterilizeable package comprising a water-proof tray having a base and at least one side wall with an upper surface, said tray being fabricated from transparent and semi-rigid plastic formed to closely receive said catheter, said inflation syringe and said three-way stopcock so as to maintain said inflation syringe and said three-way stopcock in a substantially stable position, a radial injection port having a membrane for receiving a needled injection from the loading syringe, said injection port residing within said side wall and being configured to sealingly receive said membrane of said inlet port of said three-way stopcock, and a removable package cover fabricated from a detachable section of water-proof paper, said removable package cover being adhesively attached to said upper surface of said side wall so as to create a sterile chamber within said removable cover and said tray;

a removeable port cover defining a sterilized and detachable section of water-proof paper, said removable port cover being adhesively attached to said sterlizeable package over said injection port to maintain the sterility of said chamber;

a detachable, radial, semi-rigid, and water-proof cap having a top surface and an inwardly flanged bottom surface, said cap being configured to cover said injection port upon removal of said removeable port cover from said injection port after injection of liquid radiation from the loading syringe;

a radial cap connector having a shoulder formed into said base around said radial injection port configured to receive said cap at said injection port; and a sterilized and detachable section of water-proof paper adhesively attached to said bottom surface of said cap.

17. A method for safely dispensing and delivering liquid radiation for intravascular radiation therapy using a catheter assembly, wherein the catheter assembly receives liquid radiation from a loading syringe, and then delivers that radiation energy to intraluminal tissue, said method comprising:

loading liquid radiation into the loading syringe at a radiopharmacy;

procuring a catheter assembly for performing intravascular radiation therapy, said catheter assembly comprising:

a catheter having a first end and a second end, said second end being fluidly connected to a balloon;

an inflation syringe fabricated from material which limits penetration of radiation, said inflation syringe having first and second ends, said first end slideably receiving a plunger, said inflation syringe further having a bore which fluidly connects said first and second ends and through which said plunger frictionally travels, a three-way stopcock having an inlet port for receiving an injection of liquid radiation from the loading syringe, a syringe port nondetachably and fluidly connected to said second end of said inflation syringe, and a catheter port nondetachably and fluidly connected to said first end of said catheter, said three-way stopcock further having a valve for directing the flow of liquid radiation received from the loading syringe through said three-way stopcock, said valve being oriented to place said inlet port of said stopcock and said bore of said syringe in fluid communication, and wherein said plunger of said inflation syringe has been partially withdrawn from said bore of said inflation syringe so as to pull a vacuum within said inflation syringe, thereby biasing the liquid radiation to travel into said bore of said syringe when injected from the loading syringe into said inlet port;

a sterilizeable package comprising a water-proof tray having a base and at least one side wall with an upper surface, said tray being fabricated from transparent and semi-rigid plastic formed to closely receive said catheter, said inflation syringe and said three-way stopcock so as to maintain said inflation syringe and said three-way stopcock in a substantially stable position, a radial injection port having a membrane for receiving an injection from the loading syringe, said injection port residing within said side wall and being configured to sealingly receive said membrane of said inlet port of said three-way stopcock, and a removable package cover fabricated from a detachable section of water-proof paper, said removable package cover being adhesively attached to said upper surface of said side wall so as to create a sterile chamber within said cover and said tray;

a removeable port cover defining a sterilized and detachable section of water-proof paper, said paper being adhesively attached to said sterlizeable package over said injection port to maintain the sterility within said chamber;

a stopcock cap residing within said chamber configured to cover said inlet port of said stopcock, said stopcock cap being fabricated from material which limits penetration of radiation;

a detachable, water-proof, and semi-rigid cap having a top surface and an inwardly flanged bottom surface, said cap configured to cover said injection port upon removal of said removeable port cover from said injection port after injection of liquid radiation from the loading syringe;

a cap connector having a shoulder formed into said base around said injection port configured to receive said cap at said injection port; and a sterilized and detachable section of water-proof paper adhesively attached to said bottom surface of said cap;

removing said removeable port cover from said injection port so as to expose said membrane in said injection port;

injecting liquid radiation from the loading syringe into said inlet port of said three-way stopcock through said injection port of said sterilizeable package;

confirming that the liquid radiation has entered said bore of said inflation syringe;

removing said sterilized and detachable section of water-proof paper adhesively attached to said bottom surface of said cap, snapping said cap onto said cap connector to maintain sterility within said chamber;

placing said catheter assembly into a first carrying case, said first carrying case being configured to receive said catheter assembly, said first carrying case further being made from material which is water-proof and which is impermeable to radiation, and said first carrying case bearing a label displaying a conventional symbol warning of the presence of radioactive material;

transporting said first carrying case from the radiopharmacy to an operating field where intraluminal radiation therapy is to be performed;

removing said catheter assembly from said first carrying case;

removing said removable package cover from said sterilizeable package;

removing said catheter, said inflation syringe and said three-way stopcock from said sterilizeable package;

rotating said valve of said stopcock so as to place said bore of said inflation syringe in fluid communication with said catheter only;

placing said stopcock cap over said inlet port of said stopcock;

preparing said balloon and inserting said balloon-tipped catheter into the patient in accordance with angioplasty procedures for delivery of radiation to an intraluminal treatment site;

advancing said plunger of said inflation syringe towards said second end of said inflation syringe so as to deliver an appropriate dosage of radiation to a patient's intraluminal site;

wrapping said catheter and said inflation syringe with a lead shield during delivery of radiation to the patient's intraluminal site;

removing said lead shield from around said catheter and said inflation syringe;

retracting said plunger of said inflation syringe towards said first end of said inflation syringe so as to withdraw the dosage of radiation from the patient and into said bore of said inflation syringe, thereby also obtaining a vacuum on said balloon-tipped catheter;

rotating said valve of said stopcock to prevent the flow of liquid radiation out of said bore of said inflation syringe;

removing said catheter from the patient in accordance with conventional medical procedures;

returning said catheter, said inflation syringe and said three-way stopcock to said tray of said sterilizable package;

placing said tray of said sterilizable package, along with said catheter, said inflation syringe and said three-way stopcock, into a biohazardous waste bag;

placing said biohazardous waste bag, including said tray containing said catheter, said inflation syringe and said three-way stopcock, into a second carrying case, said second carrying case being configured to receive said catheter, said inflation syringe and said three-way stopcock, said second carrying case further being made from material which is water-proof and which is impermeable to radiation, said second carrying case bearing labels displaying conventional symbols warning of the presence of both radiactive material and biohazardous waste;

transporting said second carrying case to an appropriate radio-isotope and biohazardous disposal site so that said package and its contents can be properly disposed of in their contaminated state.

\* \* \* \* \*